United States Patent [19]

Kerr

[11] 4,056,487

[45] Nov. 1, 1977

[54] VANADIUM PHOSPHORUS OXYGEN OXIDATION CATALYSTS USEFUL FOR PREPARING ANHYDRIDES FROM ALKANES

[75] Inventor: Ralph O. Kerr, Houston, Tex.

[73] Assignee: Petro-Tex Chemical Corporation, Houston, Tex.

[21] Appl. No.: 618,959

[22] Filed: Oct. 2, 1975

[51] Int. Cl.$^2$ ............................................. B01J 27/14
[52] U.S. Cl. ................................... 252/435; 252/437
[58] Field of Search ............................... 252/435, 437

[56] References Cited

U.S. PATENT DOCUMENTS

| 3,086,026 | 4/1963 | Wiebusch | 252/435 X |
|---|---|---|---|
| 3,156,706 | 11/1964 | Kerr | 252/435 X |
| 3,255,212 | 6/1966 | Kerr | 252/435 |
| 3,297,587 | 1/1967 | Scherhag et al. | 252/435 X |
| 3,736,354 | 5/1973 | Yanagita et al. | 252/437 X |
| 3,875,220 | 4/1975 | White et al. | 252/437 X |
| 3,888,886 | 6/1975 | Young et al. | 252/435 X |
| 3,895,095 | 7/1975 | Kobylinski et al. | 252/437 X |
| 3,912,763 | 10/1975 | Farha et al. | 252/435 X |

*Primary Examiner*—Winston A. Douglas
*Assistant Examiner*—John F. Niebling
*Attorney, Agent, or Firm*—Kenneth H. Johnson

[57] ABSTRACT

A catalyst complex useful for the partial oxidation of alkanes to the corresponding anhydrides, e. g., converting normal $C_4$ hydrocarbons to maleic anhydride in vapor phase, comprising as components vanadium, phosphorus, oxygen, Nb, Cu, Mo, Ni, Co and Cr. Preferred are those compositions containing in additiion one or more of Ce, Nd, Ba, Hf, U, Ru, Re, Li or Mg.

12 Claims, No Drawings

VANADIUM PHOSPHORUS OXYGEN OXIDATION CATALYSTS USEFUL FOR PREPARING ANHYDRIDES FROM ALKANES

BACKGROUND OF THE INVENTION

The present invention relates to an improved process for the preparation of dicarboxylic anhydride from $C_4$-$C_{10}$ hydrocarbons preferably using a feed containing major amounts of alkanes, by the reaction of oxygen with the hydrocarbon in vapor phase over a particular novel catalyst, such as the preparation of maleic anhydride from butane.

The production of dicarboxylic acid anhydride by catalytic oxidation of hydrocarbons is well known. The current principal route for the production of maleic anhydride is the catalytic oxidation of benzene. The direct production of maleic anhydride from $C_4$ hydrocarbons has been desirable in the past, but is now even more desirable in view of the particular world shortage of benzene. It can be readily appreciated that direct oxidation of $C_4$ hydrocarbons would be a hydrocarbon conservation, since for each mol of maleic anhydride prepared from benzene, one mol of benzene, molecular weight 78 is consumed whereas for each mol of the $C_4$ only 54 to 58 mol weight of hydrocarbon is consumed. The benzene process has consistently produced high conversions and selectivities. Although processes for the oxidation of aliphatic hydrocarbons are reported in the literature, there are certain defects and inadequacies in these processes such as short catalyst life and low yields of product. Furthermore, although many of the prior art methods are generically directed to "aliphatic" hydrocarbons, they are in all practical aspects directed to unsaturated aliphatic hydrocarbons.

A more desirable process for producing maleic anhydride would be a direct oxidation of n-butane. There are several advantages. Principal among these is the greater availability of n-butane as compared to n-butenes or butadiene. Also n-butenes may have higher economic petrochemical utilization than the n-butanes, which are now, often wastefully burned as cheap fuel.

In an early series of patents the present inventor developed a unique group of vanadium-phosphorus, oxidation catalysts, i.e., U.S. Pat. Nos., 3,156,705; 3,156,706; 3,255,211; 3,255,212; 3,255,213; 3,288,721; 3,351,565; 3,366,648; 3,385,796 and 3,484,384. These processes and catalysts proved highly efficient in the oxidation of n-butenes to maleic anhydride. Since the issuance of these pioneer patents, numerous patents have issued with various modification and improvements over the basic discoveries set forth there, e.g., U.S. Pat. Nos.: 3,856,824; 3,862,146; 3,864,280; 3,867,411; and 3,888,886.

SUMMARY OF THE INVENTION

It has now been discovered that vanadium-phosphorus-oxygen complex type catalyst modified with a particular group of components is an excellent oxidation catalyst for the conversion of $C_4$ to $C_{10}$ hydrocarbons to the corresponding anhydrides, particularly n-$C_4$ hydrocarbons to maleic anhydride. In addition to n-butane, n-butene and butadiene may also be used as feeds. The catalyst contains only a minor amount of the modifying component. The essential elements of the modifying component are Nb, Cu, Mo, Ni, Co and Cr. In addition to the essential elements the modifying component may contain one or more elements from the group of Ce, Nd, Ba, Hf, U, Ru, Re, Li or Mg. The elements comprising the modifying components are metal or metalloid in characterization.

The precise structure of the present complex catalyst has not been determined, however, the complex may be represented by formula $$V\ P_a Me_b O_x$$

wherein Me is the modifying component described above, $a$ is 0.90 to 1.3, $b$ is 0.005 to 0.4. This representation is not an empirical formula and has no significance other than representing the atom ratio of the active metal components of the catalyst. The $x$ in fact has no determinate value and can vary widely depending on the combinations within the complex. That there is oxygen present is known and the $O_x$ is representative of this.

The following listing shows the ranges of each member of the complex including the modifying component. The relative proportions are shown in atomic ratio relative to vanadium which is designated as 1. The amounts of components are selected within these ranges so that the total atoms of modifying component stays within the range given above, i.e., 0.005 to 0.4 atom per atoms of vanadium.

| Catalyst Component | Atomic Ratio |
|---|---|
| V | 1 |
| P | 0.90 – 1.3 |
| Nb | 0.001 – 0.125 |
| Cu | 0.022 – 0.201 |
| Mo | 0.0025 – 0.040 |
| Ni | 0.0022 – 0.045 |
| Co | 0.0040 – 0.066 |
| Ce | 0.0054 – 0.20 |
| Nd | 0.0022 – 0.20 |
| Cr | 0.0003 – 0.003 |
| Ba | 0.0023 – 0.0585 |
| Hf | 0.0023 – 0.409 |
| U | 0.0033 – 0.0993 |
| Ru | 0.0002 – 0.02015 |
| Re | 0.0002 – 0.0074 |
| Li | 0.0072 – 0.179 |
| Mg | 0.0088 – 0.222 |

One type of preferred catalyst contains in the modifier in addition to the essential elements one or more of (1) Ce, Nd, Ba, Hf, Ru, Re, Li or Mg, or (2) U and one or more of Ce, Nd, Ba, Hf, Ru, Re, Li or Mg.

The relative amounts of the elements in the modifier as embraced by this species are set forth above and when combined with the essential components give a total of 0.005 to 0.4 atom of modifier per atom of vanadium.

In another preferred catalyst the modifying component is Nb, Cu, Mo, Ni, Co, Cr, Ce, Nd, Ba and Hf or only Nb, Cu, Mo, Ni, Co, Cr, Ce, Nd and Ba. The amounts of modifier is in the range of 0.005 to 0.4 atom per atoms of vanadium, which may be as shown below:

| Catalyst Component | Atomic Ratio | Catalyst Component | Atomic Ratio |
|---|---|---|---|
| V | 1 | V | 1 |
| P | 0.90 – 1.3 | P | 0.90 – 1.3 |
| Nb | 0.001 – 0.125 | Nb | 0.001 – 0.125 |
| Cu | 0.022 – 0.201 | Cu | 0.022 – 0.201 |
| Mo | 0.0025 – 0.040 | Mo | 0.0025 – 0.040 |
| Ni | 0.0022 – 0.045 | Ni | 0.0022 – 0.045 |
| Co | 0.0040 – 0.066 | Co | 0.0040 – 0.066 |
| Ce | 0.0054 – 0.20 | Ce | 0.0054 – 0.20 |
| Nd | 0.0022 – 0.20 | Nd | 0.0022 – 0.20 |

-continued

| Catalyst Component | Atomic Ratio | Catalyst Component | Atomic Ratio |
|---|---|---|---|
| Cr | 0.0003 – 0.003 | Cr | 0.0003 – 0.003 |
| Ba | 0.0023 – 0.0585 | Ba | 0.0023 – 0.0585 |
| Hf | 0.0023 – 0.409 | | |

The oxygen atomic ratio may vary widely, generally in the range of 5 to 8, for the catalyst compositions of the present invention.

DETAILED DESCRIPTION OF THE INVENTION

The catalyst may be prepared in a number of ways. The catalyst may be prepared by dissolving the vanadium, phosphorus, and other components, i.e, Nb, Cu, Mo, Ni, Co, Ce, Nd, Cr, Ba, Hf, U, Ru, Re, Li or Mg in a common solvent, such as hot hydrochloric acid and thereafter depositing the solution onto a carrier. The catalyst may also be prepared by precipitating the metal compounds either with or without a carrier, from a colloidal dispersion of the ingredients in an inert liquid. In some instances the catalyst may be deposited as molten metal compounds onto a carrier; however, care must be taken not to vaporize off any of the ingredients such as phosphorus. The catalyst may also be prepared by heating and mixing anhydrous forms of phosphorus acids with vanadium compounds and compounds of the other components. The catalysts may be used as either fluid bed or fixed bed catalysts. In any of the methods of preparation heat may be applied to accelerate the formation of the complex.

One method to obtain catalysts comprises forming the catalyst complex in solution and deposited as a solution onto niobium oxide ($Nb_2O_5$). According to one solution method, the vanadium is present in solution with an average valence of less than plus 5 in the finally formed complex in solution. Preferably the vanadium has an average valency of less than plus 5 at the time the solution of catalyst complex is deposited onto the carrier, if a carrier is used. The reduced vanadium with a valence of less than 5 may be obtained either by initially using a vanadium compound wherein the vanadium has a valence of less than 5 such as vanadyl chloride, or by initially using a vanadium compound with a valence of plus 5 such as $V_2O_5$ and thereafter reducing to the lower valence with, for example, hydrochloric acid during the catalyst preparation to form the vanadium oxysalt, vanadyl chloride, in situ. The vanadium compound may be dissolved in a reducing solvent, such as hydrochloric acid, which solvent functions not only to form a solvent for the reaction, but also to reduce the valence of the vanadium compound to a valence of less than 5. Preferably, the vanadium compound is first dissolved in the solvent and thereafter the phosphorus, and other metal (metalloid) compounds are added. The reaction to form the complex may be accelerated by the application of heat. The deep blue color of the solution shows the vanadium has an average valence of less than 5. The complex formed is then, without a precipitation step, deposited as a solution onto the $Nb_2O_5$ and dried. In this procedure, the vanadium has an average valence of less than plus 5, such as about plus 4, at the time it is deposited onto the $Nb_2O_5$. Generally, the average valence of the vanadium will be between about plus 2.5 and 4.6 at the time of deposition onto the carrier.

When the above described solution method is employed, reducing agents for the vanadium may be either organic or inorganic. Acids such as hydrochloric, hydroiodic, hydrobromic, acetic, oxalic, malic, citric, formic and mixtures thereof such as a mixture of hydrochloric and oxalic may be used. Sulphur dioxide may be used. Less desirably, sulfuric and hydrofluoric acids may be employed. Other reducing agents which may be employed, but which have not been given as desirable catalysts are organic aldehydes such as formaldehyde and acetaldehyde; alcohols such as pentaerythritol, diacetone alcohol and diethanol amine. Additional reducing agents are such as hydroxyl amines, hydrazine, and nitric oxide. Nitric acid and similar oxidizing acids which would oxidize the vanadium from a valence of 4 to 5 during the preparation of the catalyst should be avoided. Generally, the reducing agents form oxysalts of vanadium. For example, if $V_2O_5$ is dissolved in hydrochloric or oxalic acid, the corresponding vanadium oxysalts are produced. These vanadium oxysalts should have as the salt forming anion, an anion which is more volatile than the phosphate anion.

Any vanadium, phosphorus and metal and metalloid compounds may be used as starting materials which when the compounds are combined and heated to dryness in air at a temperature of, for example, 300° – 350° C will leave as a deposit a catalyst complex having relative proportions within the described ranges. In the solution methods, preferred are vanadium, phosphorus and metal and metalloid (except Nb) compounds which are essentially completely soluble in boiling aqueous hydrochloric acid at 760 mm. of mercury, containing 37 percent by weight hydrochloric acid. Generally, phosphorus compounds are used which have as the cation an ion which is more volatile than the phosphate anion, for example, $H_3PO_4$. Also generally any vanadium, or Me compound which has an an anion, an anion which is either the phosphate ion or an ion which is more volatile than the phosphate anion, for example, vanadyl chloride or copper chloride, nickel chloride or the like may be used.

In the various methods of preparation any vanadium, phosphorus, metal and metalloid compounds may be used as starting materials which when the compounds are combined and heated to dryness in air at a temperature of, for example, 300° – 350° C will leave as a deposit a catalyst complex having relative proportions within the above described ranges.

In another method a solution of the vanadium component is prepared by adding a portion of a reducing agent, such as oxalic acid and isopropanol solution to a solution of water and phosphoric acid and heating this mixture to a temperature generally of around 50° – 80° C. A vanadium compound such as $V_2O_5$ is added incrementally to this heated mixture with stirring. The blue solution which indicates vanadium of average valency less than 5, is maintained by adding increments of the remaining oxalic acid-isopropanol solution. After concentration of this solution, solutions of other components are added to vanadium solution and this resultant solution concentrated to a paste-like consistency, and intimately mixed with $Nb_2O_5$, heated at moderate temperature, i.e., 200° – 400° C for a few minutes to several hours and prepared in pellets or chips.

As the source of phosphorus, various phosphorus compounds may be used, such as metaphosphoric acid, triphosphoric acid, pyrophosphoric acid, ortho-phosphoric acid, phosphorus pentoxide, phosphorus oxyiodide, ethyl phosphate, methyl phosphate, amine phosphate, phosphorus pentachloride, phosphorus trichloride, phosphorus oxybromide and the like.

Suitable vanadium compounds useful as starting materials are compounds such as vanadium pentoxide, ammonium metavanadate, vanadium trioxide, vanadyl chloride, vanadyl dichloride, vanadyl trichloride, vanadium sulfate, vanadium phosphate, vanadium tribromide, vanadyl formate, vanadyl oxalate, metavanadic acid, pyrovanadic acid, and the like. Mixtures of the various vanadium, phosphorus and metal and metalloid compounds may be used as starting materials to form the described catalyst complex.

The metal or metalloid component is also suitably introduced by employing the various compounds thereof such as the acetates, carbonates, chlorides, bromides, oxides, hydroxides, nitrates, chromates, chromites, tellurates, sulfides, phosphates and the like. The compounds are entirely conventional and those of ordinary skill in the art know these materials and can readily determine suitable compounds to prepare the catalyst, with little, if any, experimentation. A few illustrative compounds are nickel chloride, chromium sulfate, chromium trioxide, chromium chloride, barium chloride and similar compounds.

A catalyst support, if used, provides not only the required surface for the catalyst, but gives physical strength and stability to the catalyst material. The carrier or support normally has a low surface area, as usually measured, from about 0.110 to about 5 square meters per gram. A desirable form of carrier is one which has a dense non-absorbing center and a rough enough surface to aid in retaining the catalyst adhered thereto during handling and under reaction conditions. The carrier may vary in size but generally is from about 2½ mesh to about 10 mesh in the Tyler Standard screen size. Alundum particles as large as ¼ inch are satisfactory. Carriers much smaller than 10 to 12 mesh normally cause an undesirable pressure drop in the reactor, unless the catalysts are being used in a fluid bed apparatus. Very useful carriers are Alundum and silicon carbide or Carborundum. Any of the Alundums or other inert alumina carriers of low surface may be used. Likewise, a variety of silicon carbides may be employed. Silica gel may be used.

The amount of the catalyst complex on the carrier is usually in the range of about 15 to about 95 weight percent of the total weight of complex plus carrier and preferably in the range of 50 to 90 weight percent and more preferably at least 60 weight percent on the carrier. The amount of the catalyst complex deposited on the carrier should be enough to substantially coat the surface of the carrier and this normally is obtained with the ranges set forth above. With more absorbent carriers, larger amounts of material will be required to obtain essentially complete coverage of the carrier. In a fixed bed process the final particle size of the catalyst particles which are coated on a carrier will also preferably be about 2½ to about 10 mesh size. The carriers may be of a variety of shapes, the preferred shape of the carriers is in the shape or cylinder of spheres. Although more economical use of the catalyst on a carrier in fixed beds is obtained, as has been mentioned, the catalyst may be employed in fluid bed systems. Of course, the particle size of the catalyst used in fluidized beds is quite small, usually varying from about 10 to about 150 microns, and in such systems the catalyst normally will not be provided with a carrier but will be formed into the desired particle size after drying from solution.

Inert diluents may be present in the catalyst, but the combined weight of the active ingredients, e.g., vanadium, oxygen, phosphorus, metal and metalloid should preferably consist essentially of at least about 50 weight percent of the composition which is coated on the carrier, if any, and preferably these components are at least about 75 weight percent of the composition coated on the carrier, and more preferably at least about 95 weight percent.

The niobium component of the present composition is preferably niobium oxide, $Nb_2O_5$, which is intimately mixed with the other components of the catalysts, which are in solution.

In one procedure for preparing the present catalyst compositions the vanadium component is prepared by addding a portion of a reducing agent, such as an oxalic acid with or without isopropanol, to a solution of water and phosphoric acid and heating this mixture to a temperature generally around 50° – 60° C. A vanadium compound, such as $V_2O_5$ is slowly added while raising the temperature of the solution to 60° – 90° C. A blue solution indicates vanadium of average valency of less than 5 at which time the molybdenum component as $MoO_3$ is added to the solution and dissolved therein.

The V-P-Mo mixture is added to a powdered $Nb_2O_5$ and mixed together at 75° – 95° C in a suitable mixer to obtain intimate contact. The remainder of the catalyst components are added to this mixture as solutions, preferably of the chloride salts, e.g., obtained by dissolving oxides and/or carbonates in HCL.

Thus this method of catalyst preparation involves two particular aspects. First the vanadium is reduced with a reducing agent in a solution containing phosphoric acid and second, a majority (over 50% by component) of the remaining catalyst components are employed as the chloride salts. In particular Ni, Co, Cu, Cr, Nd, Ce, Ba and Hf are employed as chloride salts. All of the metal and metalloid elements employed in preparing the catalyst, with the exception of vanadium, phosphorus and niobium may be used as the chloride salt.

The resulting mixture is dried at 85° – 135° C and broken into pieces of 4 to 20 mesh and dried further at 120° – 130° C then heated at 300° C for an additional period of 0.5 to 2 or 3 hours. The catalyst may be used as such but is preferably reduced to a powder and pelleted. As noted above, binders, such as stearic acid, carriers and inert fillers may be added before pelleting.

The oxidation of the n-$C_4$ hydrocarbon to maleic anhydride may be accomplished by contacting, e.g., n-butane, in low concentrations in oxygen with the described catalyst. Air is entirely satisfactory as a source of oxygen, but synethetic mixtures of oxygen and diluent gases, such as nitrogen, also may be employed. Air enriched with oxygen may be employed.

The gaseous feed stream to the oxidation reactors normally will contain air and about 0.5 to about 2.5 mol percent hydrocarbons such as n-butane. About 1.0 to about 1.7 mol percent of the n-$C_4$ hydrocarbon are satisfactory for optimum yield of product for the process of this invention. Although higher concentrations may be employed, explosive hazards may be encountered. Lower concentrations of $C_4$, less than about one percent, of course, will reduce the total yields obtained at equivalent flow rates and thus are not normally economically employed. The flow rate of the gaseous stream through the reactor may be varied within rather wide limits but a preferred range of operations is at the rate of about 50 to 300 grams of $C_4$ per liter of catalyst per hour and more preferably about 100 to about 250 grams of $C_4$ per liter of catalyst per hour. Residence times of the gas stream will normally be less than about 4 seconds, more preferably less than about one second, and down to a rate where less efficient operations are obtained. The flow rates and residence times are calculated at standard conditions of 760 mm. of mercury and at 25° C. An improved output of maleic anhydride can be obtained with various catalysts of the prior art and with those of the present invention if the feed consists essentially of $C_4$ normal alkane, i.e., about comprising 88 to 99 or more weight percent normal $C_4$ alkane and from about 1 to 12 weight percent n-butene, benzene or a mixture thereof. A preferred feed for the catalyst of the present invention for conversion to maleic anhydride is a n-$C_4$ hydrocarbon comprising a predominant amount of n-butane and more preferably at least 90 mol percent n-butane.

A variety of reactors will be found to be useful and multiple tube heat exchanger type reactors are quite satisfactory. The tubes of such reactors may vary in diameter from about ¼ inch to about 3 inches, and the length may be varied from about 3 to about 10 or more feet. The oxidation reaction is an exothermic reaction and, therefore, relatively close control of the reaction temperature should be maintained. It is desirable to have the surface of the reactors at a relatively constant temperature and some medium to conduct heat from the reactors is necessary to aid temperature control. Such media may be Woods metal, molten sulfur, mercury, molten lead, and the like, but it has been found that eutectic salt baths are completely satisfactory. One such salt bath is a sodium nitrate-sodium nitrite-potassium nitrate eutectic constant temperature mixture. An additional method of temperature control is to use a metal block reactor whereby the metal surrounding the tube acts as a temperature regulating body. As will be recognized by the man skilled in the art, the heat exchange medium may be kept at the proper temperature by heat exchangers and the like. The reactor or reaction tubes may be iron, stainless steel, carbon-steel, nickel, glass tubes such as Vycor and the like. Both carbon-steel and nickel tubes have excellent long life under the conditions of the reactions described herein. Normally, the reactors contain a preheat zone of an inert material such as ¼ inch Alundum pellets, inert ceramic balls, nickel balls or chips and the like, present at about one-half to one-tenth the volume of the active catalyst present.

The temperature of reaction may be varied within some limits, but normally the reaction should be conducted at temperatures within a rather critical range. The oxidation reaction is exothermic and once reaction is underway, the main purpose of the salt bath or other media is to conduct heat away from the walls of the reactor and control the reaction. Better operations are normally obtained when the reaction temperature employed is no greater than about 100° C above the salt bath temperature. The temperature in the reactor, of course, will also depend to some extent upon the size of the reactor and the $C_4$ concentration. Under usual operating conditions, in compliance with the preferred procedure of this invention, the temperature in the center of the reactor, measured by thermocouple, is about 375° C to about 550° C. The range of temperature preferably employed in the reactor, measured as above, should be from about 390° C to about 460° C and the best results are ordinarily obtained at temperatures from about 410° C to about 450° C.

Described another way, in terms of salt bath reactors with carbon steel reactor tubes about 1.0 inch in diameter, the salt bath temperature will usually be controlled between about 350° C to about 450° C. Under normal conditions, the temperature in the reactor ordinarily should not be allowed to go above about 450° C for extended lengths of time because of decreased yields and possible deactivation of the novel catalyst of this invention.

The reaction may be conducted at atmospheric, super-atmospheric or below atmospheric pressure. The exit pressure will be at least slightly higher than the ambient pressure to insure a positive flow from the reaction. The pressure of the inert gases may be sufficiently high to overcome the pressure drop through the reactor.

In one utilization of the present catalyst compositions, the oxidation is carried out at 15 to 100 psig, preferably about 20 to 50 psig and more preferably about 25 to 40 psig.

Operating under pressure as described above, the temperature in the center of the reactor, measured by thermocouple is about 375° C to about 550° C with the preferred temperature range for operating according to the present invention being 430° C to 480° C and the best results are ordinarily obtained at temperatures from about 430° C to about 455° C. Described another way, in terms of salt bath reactors with carbon steel reactor tubes about 1.0 inch in diameter, the salt bath temperature will usually be controlled between about 325° C to about 440° C. Under these conditions, the temperature in the reactor ordinarily should not be allowed to go above about 450° C for extended lengths of time because of decreased yields and possible deactivation of the novel catalyst of this invention.

The maleic anhydride may be recovered by a number of ways well known to those skilled in the art. For example, the recovery may be by adsorption in suitable media, with subsequent separation and purification of the maleic anhydride.

In the following examples, percents are by weight unless otherwise specified.

The reactor used to evaluate the catalyst compositions employed 300 milliliters of catalyst packed in a 3 foot carbon steel tube, ¾ inch inside diameter (or equivalent), with inert ¼ inch Alundum pellets on top of the catalyst material to a height 1/3 of the height of the catalyst.

The reactors were encased in a 7% sodium nitrate — 40% sodium nitrite — 53% potassium nitrate eutectic mixture constant temperature salt bath. The reactor was slowly warmed to 400° C (250°-270° C air passing over catalyst) while passing a gas stream containing 0.5 to 0.7 mol percent n-butane and air over the catalyst beginning at about 280° C. The reactor outlet was maintained at 1 psig. After the reactor had reached 390° C, the catalyst was aged by passing the n-butane - air mixture therethrough for 24 hours. The n-butane - air and temperature was increased to obtain a maximum throughput. The n-butane in the feed is increased to 1.0 - 1.5 mol percent to obtain 70 - 80% conversion. The salt bath is operated at a maximum of 420° C. The maximum throughput is achieved in relation to the maximum salt bath temperature and a maximum hot spot of about 450° C. The hot spot is determined by a probe through the center of the catalyst bed. The temperature of the salt bath can be adjusted to achieve the desired relationship between the conversion and flow rates of the n-C$_4$ - air mixture. The flow rate is adjusted to about 75% conversion and the temperature relations given above. Generally, flow rates of about 70 to 120 grams of hydrocarbon feed per liter hour are used. The exit gases were cooled to about 55°- 60° C at about ½ psig. Under these conditions, about 30 - 50% of the maleic anhydride condenses out of the gas stream. A water scrubber recovery and subsequent dehydration and fractionation were used to recover and purify the remaining maleic anhydride in the gas stream after condensation. The combined maleic anhydride recovered is purified and recovered at a temperature of about 140°-165° C overhead and 165° C bottoms temperatures in a fractionator. The purified product had a purity of 99.9+ percent maleic anhydride.

In the following examples, the sources of various reactants have been identified by abreviations or initials. The following list provides the full names of the companies:

VCA = Vanadium Corporation of America
BAKER = J. T. Baker Chemical Co.
MCB = Matheson, Coleman and Bell Manufacturing Chemist
FISHER = Fisher Scientific Co.
KBI = Kawacki, Berylco Industries, Inc.
SHATTUCK = Shattuck, S and W Chemical Co., Inc.
ENGLEHARD = Englehard Industries, Inc.
B and A = Baker and Adamson Chemical Co.
TRONA = American Chemical and Potash Co.
APACHE = Apache Chemicals, Inc.
ALLIED = Allied Chemical Co.
KERR-MCGEE = Kerr-McGee Chemical Corp.

EXAMPLES 1-4

These examples demonstrate the effectiveness of the essential elements of the modifier component according to the present invention. The following method(s) were used in the preparation of the catalyst:

EXAMPLE 1

| Ingredients: | | |
|---|---|---|
| V$_2$O$_5$ | 731.829 g | CP VCA |
| P$_2$O$_5$ as | 621.7 ml. of | 85 % H$_3$PO$_4$ Baker |
| MoO$_3$ | 12.825 g | Baker |
| CuCl$_2$ . 2H$_2$O | 90.916 g | Baker |
| Ni$_2$O$_3$ | 10.688 g | MCB |
| Co$_2$O$_3$ | 11.40 g | Baker |
| CrO$_3$ | 1.425 | Fisher |
| HfO$_2$ | 28.500 | |
| Nb$_2$O$_5$ | 75.0 | KBI |
| LiCl | 8.088 | Baker |
| NH$_4$ReO$_4$ | 3.156 | Shattuck |
| RuO$_2$ | 4.275 | Englehard |

Using a 12 liter vessel, 600 grams of oxalic acid, 621.7 ml. of 85% H$_3$PO$_4$ 750 ml. of isopropyl alcohol and 8250 ml. of water were heated to 50° C with stirring. The V$_2$O$_5$ was slowly added to this mixture forming the blue vanadyl salts. After the addition was completed the mixture was refluxed for 30 minutes and then allowed to concentrate to 6 liters. The MoO$_3$ was added and concentration continued, at 3 liters volume the remaining metal compounds were added as follows:

| | | |
|---|---|---|
| Nb$_2$O$_5$ | | |
| CuCl$_2$ . 2H$_2$O | | dissolved in H$_2$O |
| Ni$_2$O$_3$ | | dissolved in HCl |
| Co$_2$O$_3$ | | dissolved in HCl |
| CrO$_3$ | | dissolved in H$_2$O |
| LiCl | | dissolved in H$_2$O |
| RuO$_2$ | | dissolved in HCl |
| NH$_4$ReO$_4$ | | dissolved in H$_2$O |
| HfO$_2$ | | |

The mixture was then stirred and heated until it became viscous, then it was poured into pyrex dishes to be dried at 85° - 135° C for 24 hours. It was then broken to pass through a 4 mesh screen, heated to 300° C over a period of five hours and held at 300 for 1 hour. The chips were then ground in a ball mill to 60 mesh and finer. The powder was mixed with 1% stearic acid and 0.5% graphite and pelleted to 1/8 by 1/8 inch size.

The catalyst was tested as described above and the results are set out below in Table I. The test run was for 1500 hours.

EXAMPLE 2.

| Ingredients: | | |
|---|---|---|
| V$_2$O$_5$ | 1010.024 g | CP VCA |
| P$_2$O$_5$ as | 866.1 ml. of | 85% H$_3$PO$_4$ |
| MoO$_3$ | 15.96 g | Baker |
| CuCl$_2$ . 2H$_2$O | 148.488 | Baker |
| NiCl$_2$ . 6H$_2$O | 40.140 | Baker |
| Co$_2$O$_3$ | 17.955 | Baker |
| CrO$_3$ | 1.995 | Fisher |
| Nb$_2$O$_5$ | 105 | KBI |
| LiCl | 8.062 | Baker |

The V$_2$O$_5$ was slowly added to a warm solution of 800 g. oxalic acid, 1 liter of isopropyl alcohol and 866.1 ml. of 85% H$_3$PO$_4$ in 11.00 liters of water. After the addition to the mixture was refluxed and concentrated at 8 liters, the MoO$_3$ was added. The CuCl$_2$.2H$_2$O, NiCl$_2$.6H$_2$O, CrO$_3$ and LiCl was dissolved separately in water while the Co$_2$O$_3$ was dissolved in 37% HCl. At the 4.0 liter level, Nb$_2$O$_5$ and the chloride solution were added. Further heating resulted in a viscous mixture which was dried on dishes. The mass was worked up as in Example 1. The pellet size was 5/32 by 5/32 inches. The catalyst was tested as above, and the results are reported in Table I.

EXAMPLE 3.

| Ingredients: | | |
|---|---|---|
| V$_2$O$_5$ | 793.121 g | CP VCA |
| P$_2$O$_5$ as | 680.4 ml. | 85% H$_3$PO$_4$ Baker |
| MoO$_3$ | 12.54 g | Baker |
| CuCl$_2$ . 2H$_2$O | 133.44 g | Baker |
| Ni$_2$O$_3$ | 11.756 | Baker |
| Co$_2$O$_3$ | 12.54 | Baker |
| CrO$_3$ | 1.567 | Fisher |
| Nd$_2$O$_3$ | 10.972 | |
| Nb$_2$O$_5$ | 82.5 | KBI |

The V$_2$O$_5$ was dissolved carefully in a 50° C solution of 630 g. oxalic acid 750 ml. isopropyl alcohol, 680.4 ml. H$_3$PO$_4$ and 8250 ml. H$_2$O. The blue solution was concentrated to 6 liters and the MoO$_3$ added and concentration continued. The remaining metal compounds were added at 3 liters. Ni$_2$O$_3$ and Co$_2$O$_3$ were dissolved first in concentrated HCl. The Nb$_2$O$_5$ was added as such. The work up was as in Example 1. Pellet size was 5/32 by 5/32 inches. The catalyst was tested as above and the results are reported in Table I.

EXAMPLE 4.

The catalyst was prepared using the ingredients and procedures as in the previous examples. The composition is shown in the following Chart A. The pellet size was 3/16 by 3/16 inches.

CHART A

| | | CATALYST COMPOSITION | | | | | | |
|---|---|---|---|---|---|---|---|---|
| Ex. | $Nb_2O_5$ W | P/V Ratio | CuO A | $MoO_3$ W | $Ni_2O_3$ W | $Co_2O_3$ W | $CrO_3$ W | Others (W) |
| 1 | 5 | 1.14 | 3 | .9 | .75 | .8 | .10 | $HfO_2$-2, $Ru_2O_3$-.3 $Re_2O_7$-.2, $Li_2O$-.2 |
| 2 | 5 | 1.14 | 3.5 | .8 | .7 | .7 | .10 | LiOH . $H_2O$-0.4 |
| 3 | 5 | 1.15 | 4.0 | .8 | .75 | .8 | .10 | $Nd_2O_3$-.7 |
| 4 | 5 | 1.14 | 4 | 1 | .8 | 1 | .12 | BaO-1, $CeO_2$-.5 $Nd_2O_3$-.5 |

W = weight ratio
A = atomic ratio

The results of butane oxidation by the previously described process are presented below in Table I.

TABLE I.

| | | Results and Conditions | | | | | | |
|---|---|---|---|---|---|---|---|---|
| | | Butane | | | | Maleic Anhydride | | |
| Catalyst | Reactor Size | Mol % Conc. | Thruput g/l cat. hr. | Temp. °C Salt | Hot Spot | Mol % Yield | Sel. | Output g/l cat. hr. |
| Ex. 1 | 1" × 9' | 1.51 | 116 | 408 | 452 | 43 | 57 | 84 |
| Ex. 2 | 1¼" × 9' | 1.30 | 92 | 412 | 448 | 47 | 61 | 73 |
| Ex. 3 | 1" × 12' | 1.48 | 94.6 | 405 | 428 | 46 | 64 | 73 |
| Ex. 4 | 1¼" × 9' | 1.48 | 100 | 397 | 436 | 43 | 62 | 72.6 |

EXAMPLES 5-13

These examples demonstrate a species of the present invention, catalyst composition and use employing the essential elements of the modifying component plus uranium and various other elements, similar to those demonstrated in Examples 1 – 4. Substantially the same catalyst preparative procedure was employed as set forth for Example 1.

EXAMPLE 5.

Preparation as in Example 1. The $MoO_3$ was added to the V-P oxalic acid solution. The Cu, Ni, Co, Nd, Ce, Ru were added as the chlorides to the concentrated vanadyl solution. $CrO_3$ and $NH_4ReO_4$ were dissolved in water first. The uranium was added in as a nitrate in water. $Nb_2O_5$ and $HfO_2$ were added as the oxides. The pellet size was 1/8 by 1/8 inches.

EXAMPLE 6.

The same procedure as Example 5 was used. $BaCl_2.2H_2O$ was employed.

EXAMPLE 7.

The same procedure as Example 5. Mg was added as the $MgCl_2.6H_2O$.

EXAMPLES 8 and 9.

Substantially as Example 5.

EXAMPLE 10.

Substantially as Example 5. $SiO_2$ added as $(EtO)_4Si$. $SiO_2$ is not considered to be an active but a carrier.

EXAMPLES 11, 12 and 13.

Substantially as Example 5.

Note that the additional components in Examples 6, 7, and 10 were added along with the Cu, Ni, Co, Nd, Ce and Ru.

The catalyst compositions are set forth below:

CHART B

| Ex. | $Nb_2O_5$ W | P/V Ratio | CuO A | $MoO_3$ W | $Ni_2O_3$ W | $Co_2O_3$ W | $CrO_3$ W | $UO_2$ W | Others (W) |
|---|---|---|---|---|---|---|---|---|---|
| 5 | 5 | 1.14 | 3.5 | 1.1 | 0.9 | 1.0 | .15 | 3 | $HfO_2$-2, $Ru_2O_5$-.3 $Re_2O_7$-.2 $CeO_2$-.7 $Nd_2O_3$-.5 |
| 6 | " | " | " | " | " | " | " | " | BaO-1 |
| 7 | " | " | " | 0.75 | 0.8 | 0.8 | .12 | 2 | MgO-1 |
| 8 | " | " | 3.0 | 1.0 | 0.8 | 0 | 0 | 4 | $Nd_2O_3$-1 |
| 9 | " | " | 5.0 | 1.0 | 0.8 | 1.0 | .15 | 3 | $Nd_2O_3$-.7 |
| 10 | 1 | " | 3.0 | 1.0 | 0.7 | 1.0 | .12 | 4 | $Nd_2O_3$-1, ($SiO_2$-5 carrier) |
| 11 | 5 | " | 3.0 | 1.1 | 1.0 | 1.0 | .15 | 2 | |
| 12 | 5 | " | 3.0 | 1.15 | 0.75 | 0 | .15 | 3 | $Ru_2O_3$-.3 |
| 13 | 5 | " | 3.0 | " | " | 1.5 | .13 | 3 | $HfO_2$-2 |

W = weight ratio
A = atomic ratio

The conditions and results of oxidation are set out below in Table II. The procedure is that described above.

TABLE II.

| | | Butane | | | | Maleic Anhydride | | |
|---|---|---|---|---|---|---|---|---|
| Catalysts | Reactor Size | Mol % Conc. | Thruput g/l cat. hr. | Temp °C Salt | Hot Spot | Mol % Yield | Sel. | Output g/l cat hr. |
| Ex. 5 | 1" × 9' | 1.32 | 120 | 396 | 446 | 45 | 61 | 91 |
| Ex. 6 | ¾" × 3' | 1.45 | 110 | 401 | 440 | 45 | 62.5 | 84 |
| Ex. 7 | ¾" × 3' | 1.43 | 98 | 419 | 456 | 47 | 63 | 78 |
| Ex. 8 | ¾" × 3' | 1.3 | 102 | 409 | 453 | 45 | 60 | 77.5 |
| Ex. 9 | ¾" × 3' | 1.3 | 100 | 406 | 444 | 45 | 63 | 76 |

TABLE II.-continued

| Catalysts | Reactor Size | Butane Mol % Conc. | Butane Thruput g/l cat hr. | Temp ° C Salt | Temp ° C Hot Spot | Maleic Anhydride Mol % Yield | Maleic Anhydride Sel. | Maleic Anhydride Output g/l cat hr. |
|---|---|---|---|---|---|---|---|---|
| Ex. 10 | ⅞" × 3' | 1.27 | 105 | 405 | 446 | 43 | 64 | 76 |
| Ex. 11 | ⅞" × 3' | 1.24 | 100 | 412 | 455 | 45 | 59 | 76 |
| Ex. 12 | 1" × 12' | 1.4 | 91 | 410 | 429 | 48 | 61 | 74 |
| Ex. 13 | 1¼" × 12' | 1.30 | 90 | 400 | 431 | 48 | 61 | 73 |

EXAMPLES 14–17

In these four runs, catalyst of the same composition as shown in Chart C were prepared by four different procedures then tested as described above.

CHART C

| Catalyst* Component | Amount |
|---|---|
| $Nb_2O_5$ | 5 wt. % |
| $V_2O_5$ | 44.85 Atomic ratio |
| $P_2O_5$ | 51.14 Atomic ratio |
| CuO | 4.00 Atomic ratio |
| $MoO_3$ | 1.00 wt. % |
| $Ni_2O_3$ | 0.80 wt. % |
| $Cu_2O_3$ | 1.00 wt. % |
| $CeO_2$ | 0.50 wt. % |
| $Nd_2O_3$ | 0.50 wt. % |
| $CrO_3$ | 0.12 wt. % |
| BaO | 1.00 wt. % |
| $H_7O_2$ | 0.80 wt. % |

*The oxide form was used for convience in demonstrating the relative amounts of actives, appropriate adjustments were made in the various preparations to produce a catalyst of this relative composition.

EXAMPLE 14. Carbonate Method

| Ingredients: | | | |
|---|---|---|---|
| $V_2O_5$ | 796.76 | g | CP Grade VCA Air Dried |
| $P_2O_5$ as | 677. | ml | 85% $H_3PO_4$ Baker |
| $MoO_3$ | 15.675 | g | Baker |
| $CuCO_3 . Cu(OH)_2$ | 86.273 | g | Fisher, Sci. |
| $NiCO_3$ | 18.000 | g | Baker |
| $CoAcetate_2 . 4H_2O$ | 47.080 | g | Baker |
| $CrO_3$ | 1.081 | g | Fisher |
| $Ba(OH)_2 . 8H_2O$ | 32.350 | g | B and A |
| $CeO_2$ | 7.837 | g | Fisher |
| $Nd_2O_3$ | 7.837 | g | Trona |
| $HfO_2$ | 12.540 | g | |
| $Cb_2O_5$ | 82.5 | g | KBI |
| The following was added to a 12 liter vessel: | | | |
| 9 liters of | | | distilled water |
| 660 g | | | Oxalic Acid Baker CP |
| 677 ml of | | | 85% $H_3PO_4$ Baker CP |

This mixture was stirred and heated to 55° C, and the $V_2O_5$ was slowly added. Heat liberated and raised the temperatures to 80° C. After all of the $V_2O_5$ was added, external heat was applied while still stirring. The excess water was evaporated off at normal pressure. At a volume of 7500 ml., the solution was blue. All of the $MoO_3$ was added to the clear blue solution at 6000 ml. This mixture was refluxed and reduced to 3 liters. At this volume the remaining active metal compounds were added:
$CuCO_2 . Cu(OH)_2$
$NiCO_3$
$CoAcetate_2 . 4H_2O$
$CrO_3$
$HfO_2$
$Ba(OH)_2$
$CeO_2$
$Nd_2O_3$
$Cb_2O_4$ This mixture was heated and stirred until it became viscous, then transferred to pyrex dishes and dried at 85°–100° and 135° C. The dried catalyst was broken up to 4 mesh and dried further at from 120° to 300° C. The calcined catalyst is next ball milled for 6 hours to less than 60 mesh. 3/16 × 3/16 inch pellets were produced using 3% graphite. The pellets were heated slowly to 300° C.

This catalyst was evaluated in 1 in. by 12 ft. tube, cooled by the eutectic salt - $KNO_3$, $NaNO_2$, $NaNO_3$. Conditions were: salt temperature of 413° C, hot spot of 427° C, head pressure of 13.8 lb., butane at 1.37 mol % and a butane throughput of 97g. butane per liter catalyst hour. Maleic anhydride was produced at 38 mol % yield with an output of 62 g. MA/liter cat. hr. The system was operated for 750 hours.

EXAMPLE 15. Acetate Method

| Ingredients: | | | |
|---|---|---|---|
| $V_2O_5$ | 796.76 | g | CP Grade VCA |
| $P_2O_5$ | 677 | ml | 85% $H_3PO_4$, Baker CP |
| $MoO_3$ | 15.675 | g | Baker |
| $CuAcetate_2 . H_2O$ | 155.80 | | Baker |
| $NiAcetate_2 . 4H_2O$ | 37.732 | | Baker |
| $CoAcetate_2 . 4H_2O$ | 47.080 | | Baker |
| $CrO_3$ | 1.881 | | Fisher |
| $BaAcetate_2$ | 26.113 | | B and A |
| $CeO_2$ | 7.837 | | Fisher |
| $NdCl_3 . 6H_2O$ | 16.709 | | Apache |
| $HfO_2$ | 12.540 | | |
| $Cb_2O_5$ | 82.5 | | KBI |

This catalyst was prepared in a manner similar to that of Example 1 except that 9000 ml. of water was used with 690 g. of oxalic acid. The $V_2O_5$ was slowly added to the solution of $H_3PO_4$ and oxalic acid with stirring at 50° to 80° C. The active metals were added to the more concentrated solution as in Example 1. The workup was the same as EXAMPLE 1, except the pellet size was 5/32 × 5/32 inch.

The catalyst was evaluated for 500 hours in a 1 inch by 12 ft. reactor. The conditions were:

| 410° C | Salt temperature |
|---|---|
| 421° C | hot spot |
| 17.8 | head pressure |
| 1.21 mol % | Butane concentration |
| 76 g | Butane/liter cat./hr. throughput |

Maleic anhydride was produced at 40 mol % yield with a 51 g. maleic anhydride liter cat. 1 hr. output.

EXAMPLE 16. Chloride Method I

| Ingredients: | | | |
|---|---|---|---|
| $V_2O_5$ | 1207.21 | g | CP Grade VCA |
| $P_2O_5$ | 1025.6 | ml | 85% $H_3PO_4$ Baker |
| $MoO_3$ | 23.750 | g | Baker |
| $CuCl_2 . 2H_2O$ | 202.3 | g | Baker dissolved in $H_2O$ |
| NiO | 17.162 | g | Baker dissolved in HCl |
| $Co_2O_3$ | 23.750 | g | Baker dissolved in HCl |
| $CrO_3$ | 2.850 | | Fisher dissolved in $H_2O$ |
| $Ba(OH)_2 . 8H_2O$ | 48.866 | | Allied dissolved in $H_2O$ |
| $CeO_2$ | 11.874 | | Fisher dissolved in HCl |
| $NdCl_3 . 6H_2O$ | 25.315 | | Apache dissolved in $H_2O$ |
| $HfO_2$ | 19.00 | | |
| $Cb_2O_5$ | 125.0 | | KBI |

The $V_2O_5$ was slowly added to a solution of 12,000 ml of $H_2O$, 1000 g. oxalic acid (Baker CP) and 1025.6 ml. of $H_3PO_4$ (Baker CP). After refluxing and digestion, the volume was reduced. At 6 liters, $MoO_3$ was added and concentration continued. The remaining metal compounds were added at 4 liters. Further heating produced a viscous liquid which was tray dried at 85° to 135° C. The catalyst mass was broken up to 4 mesh, heated further to 300° C. It was cooled and ball milled to 60 mesh. Using 3% graphite, it was pelleted in 3/16 by 3/16 inch size and evaluated in a 1¼ inch by 12 foot reactor for a total period of 900 hours. The following data was collected in oxidative dehydrogenation:

| Hours on Test | Temperature Salt | Temperature Hot Spot | Pressure PSIG | BUTANE Mol % Conc. | BUTANE Through-put g/l cat. hr. | MALEIC ANHYDRIDE Mol % Yield | MALEIC ANHYDRIDE Output g.MA/L cat./hr. |
|---|---|---|---|---|---|---|---|
| 500 | 393 | 420 | 12.3 | 1.19 | 68 | 45.5 | 52 |
| 800 | 395 | 428 | 15.2 | 1.41 | 91 | 44.5 | 68 |
| 900 | 397 | 436 | 15.3 | 1.48 | 100 | 43 | 72.6 |

EXAMPLE 17. Chloride Method II

Ingredients:

| $V_2O_5$ | 1207.21 | g | CP Grade VCA air dried |
| $P_2O_5$ | 1025.6 | ml of | 85% $H_3PO_4$ Baker |
| $MoO_3$ | 23.750 | g | Baker |
| $CuCl_2 . 2H_2O$ | 202.3 | g | Baker |
| NiO | 17.162 | g | Baker |
| $Co_2O_3$ | 23.750 | g | Baker |
| $CrO_3$ | 2.850 | g | Fisher |
| $BaCl_2 . 2H_2O$ | 37.835 | g | Baker |
| $CeO_2$ | 11.874 | g | Fisher |
| $Nd_2O_3$ | 11.874 | g | Kerr-McGee |
| $HfO_2$ | 19.00 | g | |
| $Nb_2O_5$ | 125.0 | g | KBI |

Using a total volume of 16 liters, mix the following:

| 9. | liters of distilled water | |
| 1000. | g. oxalic acid | Baker CP |
| 1000. | ml. isopropyl alcohol | Baker CP |
| 1025.6 | ml. 85% $H_3PO_4$ | Baker |

Heat the mixture to 50° – 60° C and add the $V_2O_5$ slowly while raising the temperature to 65° C to 85° C. After all of the $V_2O_5$ is added, reflux slowly until the solution is homogeneous and blue. Reduce the volume to 6 liters by taking off water and alcohol on reflux. At 6 liters, add the $MoO_3$ to the vanadyl phosphate solution and continue to reflux and reduce the volume to 4.4l. The $Nb_2O_5$ is added to a tumbler, about 20 liter size, and prewarmed to 40° – 60° C. The concentrated V-P-Mo mixture is then added to the tumbler. The heat source is increased to raise the temperatures to 75° – 90° C and held there. The NiO is dissolved in 400 ml. of HCl along with the $Co_2O_3$. The oxides are digested to the soluble chlorides while reducing the HCl volume to 200 ml. 100 ml. of $H_2O$ is added to the clear, dark solution. The Ni-Co mixture is then added to the V-P-Mo-$Nb_2O_5$ mixture in the tumbler. The $CuCl_2.2H_2O$ is dissolved in 400 ml. of $H_2O$ and is added next; followed by $CrO_3$ in 50 ml. of $H_2O$. When the mixture becomes green and slightly viscous, $Nd_2O_3$, dissolved in $H_2O$ and HCl and $CeO_2$, dissolved in concentrated HCl, are added along with $BaCl_2$ in $H_2O$. Shortly after this, the $HfO_2$ is added. After heating and loss of water vapor, the mixture becomes more viscous and difficult to stir. It is then transferred to pyrex dishes. The green mixture is dried from 85° C to 100 to 135° C over a 36-hour period. The solid mass is broken up to a 4 mesh, or less, and dried from 120° to 300° C over 4 hours; held at 300° C for one hour. The chipped catalyst is ball milled in a dry atmosphere for 6 hours to obtain 60 mesh fines. To this is mixed 0.5% Curtin type graphite and 1% Baker stearic acid. 3/16 × 3/16 inch pellets are produced. The pellets are heated slowly to 300° C so that they can be added directly to the hot salt reactor held at 250° C.

This composition gave a maleic anhydride output of 85 g MA/liter catalyst hour in a 1¼ inch by 12 foot tube at 402° C salt and 437° C hot spot, with a 1.69 mol % butane feed concentration and a yield of 43.5 mol %. At a lower output, 76 g. MA/liter catalyst hour, the yield was 46 mol % at a feed concentration of 1.46% butane.

SUMMARY OF RESULTS

EXAMPLES 14–17

TABLE III

| Ex. | Method | Maleic Yield Mol % | Anhydride Output g/l cat./hr. |
|---|---|---|---|
| 1. | Carbonate | 38 | 62 |
| 2. | Acetate | 40 | 51 |
| 3. | Chloride I | 43 | 72.6 |
| 4. | Chloride II | 45.5 | 76 |

EXAMPLE 18

A catalyst was prepared by mixing 3 liters of distilled water, 1637 g 85% $H_3PO_4$, heating to 190° F, adding 1117 g $V_2O_5$ thereto refluxing one hour at 212° F. To this mixture 927 grams of oxalic acid in 1 liter of water was added over a one hour period and the resulting mixture refluxed at 212° F until a clear blue solution was obtained (14 – 16 hours). 17.6 grams of $MoO_3$ was added to this solution and digested for 15 to 30 minutes and the volume reduced by 6 liters. A dry blend of:

108.8 g $CuCO_3.Cu(OH)_2$
22.4 g $NiCO_3$
34.0 g $CoCO_3$
25.5 g $BaCO_3$ was slowly added to the P-V-Mo solution at 205° F, followed by the addition of 1.76 grams of $CrO_3$ in 20 ml of water. Water was stripped off to remove 2.6 liters. 54.7 grams of $Ce(OH)_4$ and 22.7 grams of $Nd_2O_3$ were added and the volume of water reduced by 3.2 liters.

To this mixture was added a thick paste of 68.1 grams of $Nb_2O_5$ and water. The final mixture was dried at 364° F (184° C), micro milled to produce a product of 75% finer than 325 mesh, dry mixed, slurried with water and 4% HCl and digested for 30 minutes at 180° – 190° F. Stripped, dried at 257° F for 16 hours, crushed to less than 5 mesh and calcined at 720° F (7 minutes in hot zone of an indirect gas fired rotary kiln). Micro milled to 75% finer than 325 mesh, blended with 1.5 wt. % graphite and tableted (1/8 or 3/16 inch).

This catalyst at 406° C gave a yield of 45 mol % maleic anhydride and an output of 74.5 grams of MA per liter of catalyst per hour.

EXAMPLE 19

A catalyst according to the present invention was prepared by dissolving 263.374 g. $V_2O_5$ (CP VCA) in a solution of 2750 ml. distilled water, 210 g. oxalic acid, 228 ml. 85% $H_3PO_4$ (Baker) and 250 ml. isopropyl alcohol at 50° to 80° C. The green mixture was digested and reduced in volume. At 2 liters, 5.225 grams of $MoO_3$ was added. Heating and stirring was continued until the blue solution was concentrated to 900 ml. The following compounds were added:

| | | | |
|---|---|---|---|
| 5.5 | g | $Cb_2O_5$ | |
| 44.508 | g | $CuCl_2 \cdot 2H_2O$ | dissolved in $H_2O$ |
| 3.775 | g | NiO | dissolved in HCl |
| 5.225 | g | $Co_2O_3$ | dissolved in HCl |
| 0.627 | g | $CrO_3$ | dissolved in $H_2O$ |
| 2.612 | g | $CeO_2$ | dissolved in HCl |
| 8.324 | g | $BaCl_2 \cdot 2H_2O$ | dissolved in $H_2O$ |
| 4.180 | g | $HfO_2$ | |
| 22.00 | g | $Nd_2O_3$ | |

The mixture was heated and stirred until a paste was obtained which was transferred to dishes and dried from 85° to 135° C. This was broken up and dried further to 300° C, cooled, and ball milled to 60 mesh. To this powder 0.5% graphite and 1% stearic acid was added. It was then converted to 1/8 × 1/8 inch pellets. The results of a run using this catalyst are in Table IV.

8250 ml. $H_2O$, 660 g. oxalic acid, 780 ml. isopropyl alcohol and 683.8 ml. of 85% $H_3PO_4$ were mixed in a 12 liter reactor. The $V_2O_5$ was slowly added to this reducing medium at 50° C to 80° C. After refluxing a blue vanadyl solution was obtained which was concentrated to 6 liters. $MoO_3$ was added and concentration was continued to 3 liters. The concentrated hot solution was added to $Nb_2O_5$ in a hot tumbler. The dissolved chloride salts of Cu, Ni, Co were added, along with $CrO_3$ dissolved in water. The $CeO_2$ and $Nd_2O_3$ were dissolved in concentrated HCl and the $BaCl_2 \cdot 2H_2O$ in water. These were also added to the tumbler along with $HfO_2$. Heating and tumbling was continued until the mass became viscous but pourable. It is transferred to pyrex dishes and dried at 85° C to 135° C. The mass is broken up to 4 mesh and heated slowly to 300° C. After cooling 125° C, the material is ball milled to 60 mesh, mixed with 1% stearic acid and 0.5% graphite and pelleted to 5/32 × 5/32 inch size. It is heated to 300° C slowly in order to charge a 250° C salt reactor.

The reactor was a 1 inch by 12 foot tube of carbon steel surrounded by molten salt with adequate stirring.

TABLE IV.

| Example | $Cb_2O_5$ W | $V_2O_5$ A | $P_2O_7$ A | CuO A | $MoO_3$ W | $Ni_2O_3$ W | $Co_2O_3$ W | $CrO_3$ W | BaO W | $HfO_2$ W | $CeO_2$ W | $Nd_2O_3$ W |
|---|---|---|---|---|---|---|---|---|---|---|---|---|
| 19 | 1 | 44.44 | 51.56 | 4 | 1 | .8 | 1 | .12 | 1 | .8 | .5 | 4 |
| 20 | 1 | " | " | " | " | " | " | " | " | " | 4 | .5 |

W = weight ratio
A = atomic ratio

Conditions and results of the evaluation:

| Catalyst | Reactor, Size | Temp. ° C | | Butane | | Maleic Anhydride | |
|---|---|---|---|---|---|---|---|
| | | Salt | Hot Spot | Conc. | Thruput | Mol % Yield | Output g MA/1 cat./hr |
| Ex. 19 | ¾" × 3' | 395 | 418 | 1.13 | 78 | 45.5 | 60 |
| | | 394 | 433 | 1.35 | 125 | 40.0 | 84 |
| | | 394 | 435 | 1.55 | 140 | 39.0 | 92 |
| Ex. 20 | ¾" × 3' | 403 | 427 | 1.19 | 96 | 46 | 74.6 |
| | | 407 | 444 | 1.35 | 108 | 46 | 83.9 |

EXAMPLE 20

A second catalyst was prepared in the same manner as that of Example 19, but that the relative proportion of $CeO_2$ and $Nd_2O_3$ were reversed so that 4 wt. % $CeO_2$ and 0.5 wt. % $Nd_2O_3$ were employed. The results of a run using this composition are also set out in Table IV.

EXAMPLES 21 and 22

The examples demonstrate the use of small amounts of butene and benzene in a butane feed stream for oxidation to maleic anhydride to improve the output of the oxidation process. The catalyst employed in Example 21 was prepared by the following procedure:

EXAMPLE 21.

| Ingredients: | | | |
|---|---|---|---|
| $V_2O_5$ | 805 | g | CP VCA |
| $P_2O_5$ | 683.8 | ml | 85% $H_3PO_4$ Baker |
| $MoO_3$ | 14.107 | g | Baker |
| $CuCl_2 \cdot 2H_2O$ | 100.0 | g | Baker |
| $Ni_2O_3$ | 11.756 | g | MCB |
| $Co_2O_3$ | 12.540 | | Baker |
| $BaCl_2 \cdot 2H_2O$ | 17.480 | | Baker |
| $CrO_3$ | 1.567 | | Fisher |
| $CeO_2$ | 10.972 | | Fisher |
| $Nd_2O_3$ | 10.972 | | Kerr-McGee |
| $HfO_2$ | 31.35 | | |
| $Nb_2O_5$ | 82.5 | | KBI |

The catalyst is loaded without removing the salt. Starting at 250° C with preheated catalyst, air is slowly passed over the catalyst while heating it to 280° C. At this temperature butane is introduced at 0.5 mol % using 1/3 of the normal air flow. The temperature is slowly raised to b 300° - 320° - 340° and 360° C over a 24 to 48-hour period. The flow concentration and temperature are then raised and adjusted slowly to fully air flow and finally to full butane throughput. The butanes normally used are 400° C in a 1¼ inch tube or 410° C in the 1 inch tubes. Hot spots in these salt cooled tubes generally are in the range of 425° - 435° C which are acceptable values. Runs of 2100 hours or about three months have been made. However, the catalyst potential is usually determined after 500 to 1000 hours.

The same procedure as described above was employed for the oxidation except that the amounts of butene and/or benzene were added to the n-butane stream. The results are given below in Table V.

The yield is determined by weighing the butane used in a 24-hour period and isolating the product. The maleic acid solution which is water clear is analyzed for maleic by liberation of an adequate sample. The exit gas is analyzed for unreacted butane and CO + $CO_2$ by gas chromatographic means.

The catalyst of Example 22 was that described in Example 3. The catalyst composition compare as follows:

CHART D
CARRIER ACTIVES

| Catalyst | Cb$_2$O$_5$ W | V$_2$O$_5$ A | P$_2$O$_5$ A | CuO A | MoO$_3$ W | Ni$_2$O$_3$ W | Co$_2$O$_3$ W | CrO$_3$ W | CeO$_2$ W | Nd$_2$O$_3$ W | HfO$_2$ W | BaO W |
|---|---|---|---|---|---|---|---|---|---|---|---|---|
| Ex. 21 | 5 | 45.33 | 51.67 | 3 | .9 | .7 | .8 | .1 | .7 | .7 | 2 | .7 |
| Ex. 22 | 5 | 44.63 | 51.37 | 4 | .8 | .75 | .8 | .1 | | .7 | | |

W = weight ratio
A = atomic ratio

TABLE V.

| Catalyst | Temp °C | | Butane | | Butene | | Benzene | | Maleic Anhydride | | |
|---|---|---|---|---|---|---|---|---|---|---|---|
| | Salt | Hot Spot | Conc. Mol % | Thruput g/l cat hr | Conc. Mol % | Thruput g/l cat hr | Conc. Mol % | Thruput g/l cat hr | Mol % Yield | Sel | Output g/l cat.hr. |
| Ex. 21 | 408 | 417 | 1.31 | 90 | 0 | 0 | 0 | 0 | 47 | 63 | 71 |
| | 410 | 426 | 1.35 | 99 | 0.19 | 13 | 0 | 0 | 44 | 61 | 80 |
| | 410 | 427 | 1.31 | 98 | 0.161 | 11.5 | 0.158 | 15.9 | 45.5 | 62 | 91 |
| Ex. 22 | 405 | 428 | 1.48 | 95 | 0 | 0 | 0 | 0 | 46 | 64 | 73 |
| | 408 | 428 | 1.49 | 05.2 | 0 | 0 | 0.29 | 24.9 | 44.5 | 62 | 85.5 |
| | 408 | 428 | 1.47 | 94.8 | 0 | 0 | 0.43 | 37.3 | 42.8 | 61.1 | 88.6 |

Butane was extensively employed in the present examples because of its availability and easy handling. The other C$_4$ - C$_{10}$ hydrocarbons, particularly normal paraffins and olefins, also are suitable for use in conjunction with the present catalyst to produce anhydrides, for example, n-pentane, n-hexane, n-heptane, n-octane, n-nonane and n-decane and the corresponding olefins.

The invention claimed is:

1. A catalyst composition for use in the partial oxidation to C$_4$ to C$_{10}$ alkane hydrocarbons to anhydrides consisting of vanadium, phosphorus, oxygen and a modifying component consisting of the elements Nb, Cu, Mo, Ni, Co and Cr or the elements Nb, Cu, Mo, Ni, Co and Cr and one or more of the elements selected from the group of Ce, Nd, Ba, Hf, U, Ru, Re, Li, or Mg wherein the atomic ratio of vanadium:phosphorus:modifying component is 1:0.90 to 1.3:0.005 to 0.4, respectively.

2. The catalyst composition according to claim 1 wherein the atomic ratio of vanadium:phosphorus:Nb:Cu:Mo:Ni:Co:Ce:Nd:Cr:Ba:Hf:U:Ru:Re:Li:Mg is 1:0.9 to 1.3:.001 to 0.125:0.022 to 0.201:0.0025 to 0.040:0.0022 to 0.045:0.004 to 0.066:0.0054 to 0.20:0.0022 to 0.20:0.0003 to 0.003:0.0023 to 0.0585:0.0023 to 0.0409:0.0033 to 0.0993:0.0008 to 0.020:0.0002 to 0.0074:0.0072 to 0.179:0.0088 to 0.222, respectively, the total atomic ratio of Nb, Cu, Mo, Ni, Co, Ce, Nd, Cr, Ba, Hf, U, Ru, Re, Li and Mg and being in the range s of 0.005 to 0.4.

3. A catalyst composition for use in the partial oxidation of C$_4$ to C$_{10}$ alkane hydrocarbons to anhydrides consisting of vanadium, phosphorus and oxygen and a modifying component of Nb, Cu, Mo, Ni, Co, Ce, Nd, Cr, Ba and Hf or Nb, Cu, Mo, Ni, Co, Ce, Nd, Cr and Ba, wherein the atomic ratio of vanadium:phosphorus:modifying component is 1:0.90 to 1.3:0.005 to 0.4, respectively.

4. The catalyst composition according to claim 3 wherein the modifying component is Nb, Cu, Mo, Ni, Co, Ce, Nd, Cr, Ba and Hf.

5. The catalyst composition according to claim 3 wherein the modifying component is Nb, Cu, Mo, Ni, Co, Ce, Nd, Cr and Ba.

6. The catalyst composition according to claim 4 wherein the atomic ratio of vanadium:phosphorus:Nb:Cu:Mo:Ni:Co:Ce:Nd:Cr:Ba:Hf is 1:0.90 to 1.3:.001 to 0.125:0.022 to 0.201:0.0025 to 0.040:0.0022 to 0.045:0.0040 to 0.066:0.0054 to 0.2:0.0022 to 0.20:0.0003 to 0.003:0.0023 to 0.0585:0.0023 to 0.0409, respectively, the total atomic ratio of Nb, Cu, Mo, Ni, Co, Ce, Nd, Cr, Ba and Hf being in the range of 0.005 to 0.4.

7. The catalyst composition according to claim 5 wherein the atomic ratio of vanadium:phosphorus:Nb:Cu:Mo:Ni:Co:Ce:Nd:Cr:Ba is 1:0.90 to 1.3:0.001 to 0.125:0.022 to 0.040:0.0022 to 0.045:0.0040 to 0.066:0.0054 to 0.20:0.0022 to 0.20:0.0003 to 0.003:0.0023 to 0.0585, respectively, the total atomic ratio of Nb, Cu, Mo, Ni, Co, Ce, Nd, Cr and Ba being in the range of 0.005 to 0.4.

8. A catalyst composition for use in the partial oxidation of C$_4$ to C$_{10}$ alkane hydrocarbons to anhydrides consisting of vanadium, phosphorus and oxygen and a modifying component of Nb, Cu, Mo, Ni, Co and Cr and (1) one or more of the elements selected from the group consisting of Ce, Nd, Ba, Hf, Ru, Re, Li and Mg or (2) U and one or more of the elements selected from the group consisting of Ce, Nd, Ba, Hf, Ru, Re, Li and Mg, wherein the atomic ratio of vanadium:phosphorus:modifying component is 1:0.90 to 1.3:0.005 to 0.4, respectively.

9. The catalyst composition according to claim 8 wherein the modifying component is Nb, Cu, Mo, Ni, Co, Cr and one or more of Ce, Nd, Ba, Hf, Ru, Re, Li or Mg.

10. The catalyst composition according to claim 8 wherein the modifying component is Nb, Cu, Mo, Ni, Co, Cr, U and one or more of Ce, Nd, Ba, Hf, Ru, Re, Li or Mg.

11. The catalyst composition according to claim 9 wherein the atomic ratio of vanadium:phosphorus:Nb:Cu:Mo:Ni:Co:Cr:Ce:Nd:Ba:Hf:Ru:Re:Li:Mg is 1:0.90 to 1.3:0.001 to 0.125:0.022 to 0.201:0.0025 to 0.04:0.0022 to 0.045:0.004 to 0.066:0.0003 to 0.003:0.0054 to 0.20:0.0022 to 0.20:0.0023 to 0.0585:0.0023 to 0.409:0.0002 to 0.02015:0.0002 to 0.0074:0.0072 to 0.179:0.0088 to 0.222, respectively, the total atomic ratio of Nb, Cu, Mo, Ni, Co, Cr, Ce, Nd, Ba, Hf, Ru, Re, Li and Mg being in the range of 0.005 to 0.4.

12. The catalyst composition according to claim 10 wherein the atomic ratio of vanadium:phosphorus:Nb:Cu:Mo:Ni:Co:Cr:U:Ce:Nd:Ba:Hf:Re:Li:Mg is 1:0.90 to 1.3:0.001 to 0.125:0.022 to 0.201:0.0025 to 0.04:0.0022 to 0.045:0.004 to 0.066:0.0003 to 0.003:0.0033 to 0.0993:0.0054 to 0.20:0.0022 to 0.20:0.0023 to 0.0585:0.0023 to 0.0409:0.0002 to 0.0074:0.0072 to 0.179:0.0088 to 0.222, respectively, the total atomic ratio of Nb, Cu, Mo, Ni, Co, Cr, U, Ce, Nd, Ba, Hf, Re, Li and Mg being in the range of 0.005 to 0.4.

* * * * *

UNITED STATES PATENT OFFICE
CERTIFICATE OF CORRECTION

PATENT NO. : 4,056,487            Page 1 of 2
DATED : November 1, 1977
INVENTOR(S) : Ralph O. Kerr It is certified that error appears in the above—identified patent and that said Letters Patent are hereby corrected as shown below:

Column 1, line 51 reads "modification" but should read -- modifications --

Column 5, line 60 reads "or cylinder of spheres" but should read -- of cylinder or spheres --

Column 6, line 30 reads "HCL" but should read -- HCl --

Column 7, line 12 reads "about comprising" but should read -- comprising about --

Column 14, line 16 reads "in 1 in." but should read -- in a 1 in. --

Column 16, line 1 reads "pyrex" but should read -- Pyrex --

Column 17, line 50 reads "The examples" but should read -- These examples --

Column 18, line 14 reads "pyrex" but should read -- Pyrex --

UNITED STATES PATENT OFFICE
CERTIFICATE OF CORRECTION

PATENT NO. : 4,056,487

DATED : November 1, 1977

INVENTOR(S) : Ralph O. Kerr

It is certified that error appears in the above-identified patent and that said Letters Patent are hereby corrected as shown below:

Column 18, line 48 reads "fully" but should read -- full --

Signed and Sealed this

Twenty-sixth Day of February 1980

[SEAL]

Attest:

SIDNEY A. DIAMOND

Attesting Officer

Commissioner of Patents and Trademarks